United States Patent

Schmidt et al.

[11] 3,931,359
[45] Jan. 6, 1976

[54] O-(4-IODOPHENYL) THIONO (PHOSPHONIC ACID ESTERS AND ESTER AMIDES

[75] Inventors: Karl-Julius Schmidt, Wuppertal; Bernhard Homeyer, Opladen; Ingeborg Hammann, Cologne; Wilhelm Stendel, Wuppertal, all of Germany

[73] Assignee: Bayer Aktiengesellschaft, Leverkusen, Germany

[22] Filed: Jan. 9, 1973

[21] Appl. No.: 322,262

[30] Foreign Application Priority Data
  Jan. 20, 1972  Germany.......................... 2202528

[52] U.S. Cl. ............... 260/959; 260/961; 260/964; 424/220; 424/222; 424/225
[51] Int. Cl.².. A01N 9/36; C07F 9/205; C07F 9/24; C07F 9/40
[58] Field of Search.................... 260/959, 961, 964

[56] References Cited
UNITED STATES PATENTS

| | | | |
|---|---|---|---|
| 2,552,538 | 5/1951 | Drake et al..................... | 260/959 X |
| 2,552,574 | 5/1951 | Moyle et al...................... | 260/959 |
| 2,875,233 | 2/1959 | Blair et al....................... | 260/959 X |
| 3,149,143 | 9/1964 | Newallis et al. .................... | 260/961 |
| 3,253,061 | 5/1966 | Schlor et al..................... | 260/961 X |
| 3,260,712 | 7/1966 | Schrader......................... | 260/959 X |
| 3,322,864 | 5/1967 | Schrader......................... | 260/964 X |
| 3,444,274 | 5/1969 | Schrader......................... | 260/964 X |

OTHER PUBLICATIONS
Derwent Japanese Patents Report, Vol. 4, No. 41, page 9, 23038/65.

*Primary Examiner*—Richard L. Raymond
*Attorney, Agent, or Firm*—Burgess, Dinklage & Sprung

[57] ABSTRACT

O-(4-iodophenyl) (thiono) phosphoric (phosphonic) acid esters and ester amides of the formula

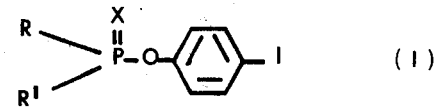

in which
  R is an alkoxy, monoalkylamino or dialkylamino radical with 1–6 carbon atoms per alkyl group,
  R' is a phenyl radical, an alkyl radical with 1–6 carbon atoms, a monoalkylamino or dialkylamino radical with 1–6 carbon atoms per alkyl group, or an alkoxy radical with 3–6 carbon atoms, and
  X is oxygen or sulfur,
which possess insecticidal and acaricidal properties.

4 Claims, No Drawings

O-(4-IODOPHENYL) THIONO (PHOSPHONIC ACID ESTERS AND ESTER AMIDES

The present invention relates to and has for its objects the provision of particular new O-(4-iodophenyl) (thiono) phosphoric (phosphonic) acid esters and ester amides, i.e. 4-iodophenol esters of phosphoric acid esters or phosphoric acid ester mono-amides or diamides, 4-iodophenol esters of O-alkyl-alkane- or -benzene-phoshonic acid esters or of N-alkyl-alkane- or -benzene-phosphonic acid amides, and their thiono analogues, which posses insecticdal or acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known that O,O-diethyl-O-(4-iodophenyl)-thionophosphoric acid ester (Compound A) possesses insecticidal properties; furthermore O,O-diethyl-O-(p-iodophenyl)-phosphoric acid ester (Compound B) has also been described in the literature (see N. N. Melnikov, Z.obsh.Khim. (*Journal of General Chemistry* (U.S.S.R.)) 23, 1357–1364 (1953); C. van Hooidonk et al., *Rec. Trav. Chim. Pays-Bas* 86 (5), 449–457 (1967)).

The present invention provides, as new compounds, the idophenyl(thiono-)phosphoric(phosphonic) acid esters, ester amides and ester diamides of the general formula

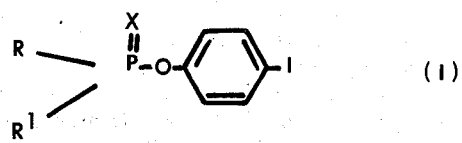

in which:
R is an alkoxy, monoalkylamino or dialkylamino radical with 1–6 carbon atoms per alkyl group,
R' is a phenyl radical, an alkyl radical with 1–6 carbon atoms, a monoalkylamino or dialkylamino radical with 1–6 carbon atoms per alkyl group, or an alkoxy radical with 3–6 carbon atoms, and
X is oxygen or sulfur.

Surprisingly, the iodophenyl(thiono-)phosphoric(phosphonic) acid esters, ester amides and ester diamides according to the invention show, besides a good acaricidal activity, a considerably higher insecticidal, especially soil-insecticidal activity than prior-art compounds of analogous structures and similar directions of activity. The compounds according to the present invention have given especially good results in the control of pests harmful to health and pests of stored products, and ectoparasites. The compounds according to the invention therefore represent a genuine enrichment of the art.

Moreover, the compounds according to the invention contribute to the reduction of the great requirement for new active compounds in the field of pesticides. This requirement originates in that ever higher demands are being made of the commercially available agents, especially in view of questions of environment protection, such as low toxicity to warm-blooded animals and low phytotoxicity, rapid degradation in and on the plant with small minimum intervals to be observed between spraying with pesticide and harvesting, and effectiveness against resistant pests.

In formula (I) R is preferably a straight or branched lower alkoxy radical with 1–4 carbon atoms or a mono-lower alkylamino or di-lower alkylamino radical with 1–3 carbon atoms per alkyl group; R' is preferably a phenyl, methyl, ethyl, n-propoxy or isopropoxy radical or a mono-lower alkylamino or di-lower alkylamino radical with 1–3 carbon atoms per alkyl residue.

The present invention also provides a process for the preparation of an iodophenyl(thiono-)phosphoric(-phosphonic) acid ester, ester amide or ester diamide of the formula (I), in which 4-iodophenol, which has the formula

is reacted, as such in the presence of an acid-binding agent or in the form of an alkali metal salt or alkaline earth metal salt thereof, with a (thiono-)phosphoric(-phosphonic) acid ester halide, ester amide halide or diamide halide of the general formula

in which:
R, R' and X have the meanings stated above, and Hal is halogen, preferably chlorine.

If O-ethylethanephosphonic acid ester chloride and 4-iodophenol are used as the starting materials, the reaction course can be represented by the following formula scheme:

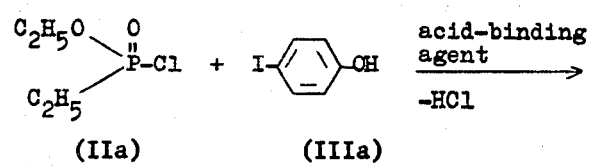

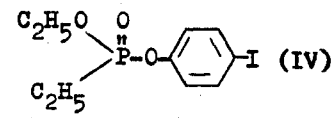

As examples of the (thiono-)phosphoric(phosphonic) acid ester halides, ester amide halides and diamide halides of the formula (II) there may be mentioned: O,O-dipropyl-, O,O-di-isopropyl- and O-propyl-O-butyl-phosphoric acid ester chlorides and their thiono analogues; O-methyl-, O-ethyl-, O-propyl-, O-isopropyl-, O-n-butyl-, O-isobutyl-, O-sec.-butyl-, O-tert.-butyl-methane-(or ethane- or benzene-) phosphonic acid ester chlorides and the corresponding thiono analogues; O-methyl-, O-ethyl-, O-n-propyl-, O-isopropyl-, O-n-butyl-, O-isobutyl-, O-sec.-butyl- and O-tert.-butyl-N-methyl- (or N-ethyl-, N-n-propyl- or N-isopropyl-) phosphoric acid ester amide chlorides and the corresponding N,N-dialkylamino compounds and the thiono analogues; N-methyl-, N-ethyl-, N-n-propyl-, N-isopropyl-methane- (or ethane- or benzene-) phosphonic acid amide chlorides, the corresponding dialkylamino and thiono compounds; N,N'-dimethyl-, N,N'-diethyl-, N,N'-di-n-propyl- and N,N'-di-isopropyl-phosphoric acid diamide chlorides and the corresponding N,N,N',N'-tetraalkyl and thiono compounds.

The (thiono)phosphoric(phosphonic) acid ester halides, ester amide halides and diamide halides used as starting materials are described in the literature and can also be prepared on an industrial scale. Iodophenol is likewise readily accessible according to known processes, for example by diazotization of p-aminophenol and reaction with potassium iodide.

The preparative process is preferably carried out with the use of a suitable solvent or diluent. As such, practically all inert organic solvents are suitable, especially aliphatic and aromatic optionally chlorinated hydrocarbons, such as benzene, toluene, xylene, benzine, methylene chloride, chloroform, carbon tetrachloride or chlorobenzene; ethers, such as diethyl ether, dibutyl ether or dioxane; ketones, for example acetone, methyl ethyl ketone, methyl isopropyl ketone or methyl isobutyl ketone; and nitriles, such as acetonitrile or propionitrile.

As acid-binding agents all customary acid-acceptors can be used. Particularly good results have been obtained with alkali metal carbonates and alcoholates, such as sodium or potassium carbonate, methylate or ethylate; however, aliphatic, aromatic or heterocyclic amines, for example triethylamine, dimethylamine, dimethylaniline, dimethylbenzylamine or pyridine can be used.

The reaction temperatures can be varied within a fairly wide range. In general, the reaction is effected at about 10° to 100°C, preferably at about 65° to 80°C. The reaction is preferably carried out under normal pressure.

For the carrying out of the process, the starting materials are preferably used in equimolar amounts, with the use of one of the aforesaid solvents, in the presence of an acid acceptor. An excess of one or other reactant brings no substantial advantages. In most cases, the procedure followed when carrying out the process is that the iodophenol in one of the solvents stated above is heated for a short time at an elevated temperature together with the acid acceptor, and the phosphoric acid derivative is then added dropwise, with stirring. After one to several hours' stirring, the reaction mixture is taken up in an organic solvent, for example benzene, the soluble constituents are washed out, the organic phase is dried and the solvent is removed by distillation under reduced pressure.

The compounds according to the invention are obtained in most cases in the form of colorless to slightly yellow-colored oils, some of which cannot be distilled without decomposition but can, by so-called "slight distillation", that is by longer heating to a moderately elevated temperature under reduced pressure, be freed from the last volatile components and in this way be purified. For the characterization of such products the refractive index is suitable; the compounds obtained in crystalline form may be characterized by their melting points.

As already mentioned, the iodophenyl(thiono-)phosphoric-(phosphonic) acid esters, ester amides and ester diamides of this invention are distinguished by an outstanding insecticidal and acaricidal effectiveness against crop pests, pests harmful to health and pests of stored products, as well as ectoparasites. They possess a good activity both against sucking and biting insects and mites (Acarina). At the same time, they exhibit a low phytotoxicity.

For these reasons, the compounds according to the invention may be used with success as pesticides in crop protection and the protection of stored products, as well as in the hygiene field.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the current gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuehniella*) and the greater wax moth (*Galleria mellonella*).

Also to be classed with the biting insects are beetles (Coleoptera), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius = Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes spec.*) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Acheta domesticus*); termites such as the eastern subterranean termite (*Reticultitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*), further, gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are classed, in particular, the spider mites (Tetranychidae) such as the two-spotted spider mite (*Tetranychus urticae*) and the European red mite (*Paratetranychus pilosus = Panonychus ulmi*), gall mites, for example the black currant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the compounds of this invention are also distinguished by an outstanding residual activity on wood and clay, as well as a good stability to alkali or limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryls sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or rodenticides, fungicides, bactericides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

Critical concentration test / soil insects

Test insect: cabbage root fly maggots (*Phorbia brassicae*)
Solvent: 3 parts by weight acetone
Emulsifier: 1 part by weight alkylarylpolyglycol ether To produce a suitable preparation of active compound, 1 part by weight of active compound is mixed with the stated amount of solvent, the stated amount of emulsifier is added and the concentrate is diluted with water to the desired concentration. The preparation of active compound is intimately mixed with soil. The concentration of the active compound in the preparation is of practically no importance; only the amount by weight of active compound per unit volume of soil, which is given in p.p.m. (for example mg/l) is decisive. The soil is filled into pots and the pots are left to stand at room temperature. After 24 hours, the test insects are put into the treated soil, and after a further 48 hours the degree of effectiveness of the active compound is determined as a percentage by counting the dead and living test insects. The degree of destruction is 100% when all the test insects have been killed; it is 0% when exactly as many test insects are alive as in the case of the control.

The active compounds, the amounts applied and the results can be seen from the following Table 1:

Table 1

| Active compound | (Test with *Phorbia brassicae* maggots in the soil) Degree of destruction in % with a concentration of active compound of | | | | | |
|---|---|---|---|---|---|---|
| | 20 | 10 | 5 | 1.5 | 1.25 | 0.625 ppm |
| (5) I-C₆H₄-O-P(=S)(OC₂H₅)(C₂H₅) | 100 | 100 | 100 | 100 | 100 | 50 |
| (4) I-C₆H₄-O-P(=S)(CH₃)(OC₂H₅) | 100 | 100 | 100 | 95 | 50 | |
| (1) I-C₆H₄-O-P(=S)(CH₃)(OC₃H₇-i) | 100 | 100 | 80 | 50 | | |
| (6) I-C₆H₄-O-P(=S)(C₂H₅)(OC₃H₇-i) | 100 | 100 | 50 | | | |

Table 1-continued (Test with *Phorbia brassicae* maggots in the soil)

| Active compound | Degree of destruction in % with a concentration of active compound of | | | | | |
|---|---|---|---|---|---|---|
| | 20 | 10 | 5 | 1.5 | 1.25 | 0.625 ppm |

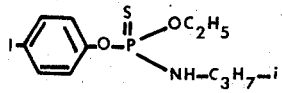

(8)

| | 100 | 100 | 100 | 50 | | |

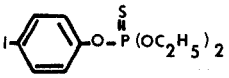

(A)     (known)

| | | 50 | 0 | | | |

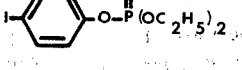

(B)     (known)

| | | | 0 | | | |

EXAMPLE 2

Drosophila test

Solvent: 3 parts by weight alkylarylpolyglycol ether
Emulsifier: 1 part by weight acetone To produce a suitable preparation of active compound, 1 part by weight of the active compound is mixed with the stated amount of solvent containing the stated amount of emulsifier, and the concentrate is diluted with water to the desired concentration.

1 ml of the preparation of the active compound is applied with a pipette to a filter paper disc of 7 cm diameter. The wet disc is placed in a glass vessel containing 50 vinegar flies (*Drosophila melanogaster*) and covered with a glass plate.

After the specified periods of time, the destruction is determined as a percentage: 100% means that all the flies are killed; 0% means that none of the flies are killed.

The active compounds, their concentrations, the evaluation times and the degree of destruction can be seen from the following Table 2:

Table 2

(*Drosophila* Test)

| Active compound | Concentration of active compound in % by weight | Degree of destruction in % after 1 day |
|---|---|---|
| 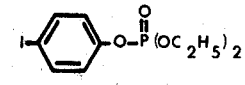 (B)   (known) | 0.1<br>0.01 | 20<br>0 |

Table 2-continued
(*Drosophila* Test)

| Active compound | Concentration of active compound in % by weight | Degree of destruction in % after 1 day |
|---|---|---|
| 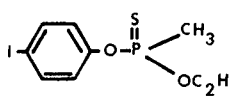 (4) | 0.1<br>0.01<br>0.001 | 100<br>100<br>99 |
| 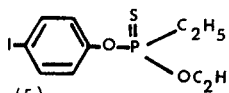 (5) | 0.1<br>0.01<br>0.001 | 100<br>100<br>99 |
| 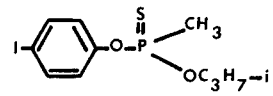 (1) | 0.1<br>0.01<br>0.001 | 100<br>100<br>55 |
| 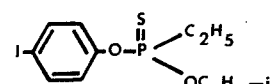 (6) | 0.1<br>0.01<br>0.001 | 100<br>100<br>60 |
| 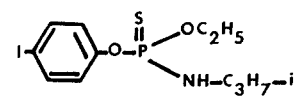 (8) | 0.1<br>0.01 | 100<br>90 |

EXAMPLE 3

Myzus test (contact action)
Solvent: 3 parts by weight acetone
Emulsifier: 1 part by weight alkylarylpolyglycol ether To produce a suitable preparation of active compound, 1 part by weight of the active compound is mixed with the stated amount of solvent containing the stated amount of emulsifier and the concentrate is diluted with water to the desired concentration.

Cabbage plants (*Brassica oleracea*) that have been heavily infested with peach aphids (*Myzus persicae*) are sprayed with the preparation of the active compound until dripping wet.

After the specified periods of time, the degree of destruction is determined as a percentage: 100% means that all the aphids are killed whereas 0% means that none of the aphids are killed.

The active compounds, the concentrations of the active compounds, the evaluation times and the results can be seen from the following Table 3:

Table 3
*Myzus* test

| Active Compound | Concentration of active compound in % by weight | Degree of destruction in % after 1 day |
|---|---|---|
|  (B) (known) | 0.1<br>0.01 | 50<br>0 |
| 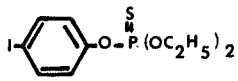 (A) (known) | 0.1 | 0 |

Table 3-continued

| Active Compound | *Myzus* test Concentration of active compound in % by weight | Degree of destruction in % after 1 day |
|---|---|---|
| 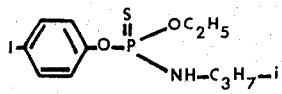 (8) | 0.1 0.01 | 100 100 |

EXAMPLE 4

Tetranychus test (resistant)
Solvent: 3 parts by weight acetone
Emulsifier: 1 part by weight alkylarylpolyglycol ether To produce a suitable preparation of active compound, 1 part by weight of the active compound is mixed with the stated amount of solvent containing the stated amount of emulsifier and the concentrate so obtained is diluted with water to the desired concentration.

Bean plants (*Phaseolus vulgaris*) that have a height of approximately 10–30 cm are sprayed with the preparation of the active compound until dripping wet. These bean plants are heavily infested with the two-spoted spider mite (*Tetranychus urticae*) in all stages of development.

After the specified periods of time, the effectiveness of the preparation of active compound is determined by counting the dead mites. The degree of destruction thus obtained is expressed as a percentage: 100% means that all the spider mites are killed whereas 0% means that none of the spider mites are killed.

The active compounds, the concentrations of the active compounds, the evaluation times and the results can be seen from the following Table 4:

Table 4

| (*Tetranychus* test/resistant) Active compound | Concentration of active compound in % by weight | Degree of destruction in % after 2 days |
|---|---|---|
| 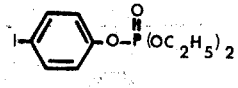 (B) (known) | 0.1 | 0 |
| 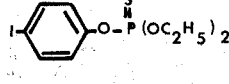 (A) (known) | 0.1 | 0 |
| 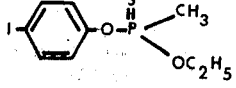 (4) | 0.1 | 80 |

Table 4-continued

| Active compound | (*Tetranychus* test/resistant) Concentration of active compound in % by weight | Degree of destruction in % after 2 days |
| --- | --- | --- |
| 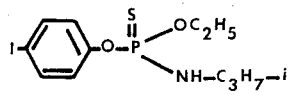 (8) | 0.1 | 100 |
| 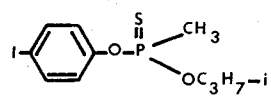 (1) | 0.1 | 90 |

EXAMPLE 5

Test with parasitizing fly larvae
Solvent: 35 parts by weight ethyleneglycolmonomethyl ether
Emulsifier: 35 parts by weight nonylphenolpolyglycol ether To produce a suitable preparation of active compound, 30 parts by weight of the active compound concerned are mixed with the stated amount of solvent which contains the proportion stated above of emulsifier, and the concentrate so obtained is diluted with water to the desired concentration.

About 20 fly larvae (*Lucilia cuprina*) are put into a test-tube which contains about 2 ml of horse musculature. 0.5 ml of the preparation of active compund is applied to this horseflesh. After 24 hours, the degree of destruction is determined as a percentage: 100% means that all, and 0% that none, of the larvae have been killed.

The active compounds investigated, the concentrations tested and the findings obtained can be seen from the following Table 5:

Table 5

| Active compound | (Test with parasitizing fly larvae) Concentration of active compound in ppm (by weight) | Degree of destruction in % |
| --- | --- | --- |
| (5) | 100<br>30<br>10<br>3<br>1 | 100<br>100<br>100<br>100<br>0 |
| (6) | 100<br>30<br>10<br>3<br>1 | 100<br>100<br><50<br><50<br>0 |
| (8) | 100<br>30<br>10<br>3<br>1 | 100<br>100<br>100<br><50<br>0 |

The process of this invention is illustrated by the following preparative Examples.

EXAMPLE 6 a. The 4-iodophenol to be used as a starting material can be prepared, for example, as follows:

 (III)

To 109 g (1 mole) of 4-aminophenol in 500 ml of water there are added 500 g of ice; first 65 ml of concentrated sulfuric acid and then, at 0°C, a solution of 72 g of sodium nitrite in 150 ml of water are added dropwise to the reaction mixture. After addition of the total amount of the nitrite, the mixture is stirred for a further 20 minutes at 0°C and a further 20 ml of concentrated sulfuric acid are then added. This mixture is added dropwise to a solution of 200 g of potassium iodide in 200 ml of water. 1 g of copper powder is added, and the mixture is slowly heated to 75° to 80°C; nitrogen escapes. Subsequently, the reaction mixture is extracted three times with, in each case, 200 ml of chloroform. The combined chloroform extracts are washed with a 10%-strength aqueous solution of sodiuim thiosulfate, the solvent is evaporated, and the residue is distilled. After recrystallization from ligroin, 158 g (72% of theory) of 4-iodophenol of melting point 93° to 94°C are obtained.

b) 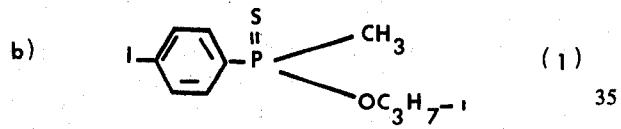 (1)

66 g (0.3 mole) of 4-iodophenol are boiled for 30 minutes with 42 g of potassium carbonate in 400 ml of acetonitrile. 51.8 g (0.3 mole) of O-isopropylmethanethionophosphonic acid ester chloride are subsequently added dropwise to the mixture, which is then heated for a further 2 hours under reflux; the reaction mixture is then taken up in 400 ml benzene, and the soluble components are washed out with water, a 1N solution of sodium hydroxide and again with water. The organic phase is dried over sodium sulfate, and the solvent is distilled off under reduced pressure. The O-isopropyl-O-(4-iodophenyl)-methanethionophosphonic acid ester remains behind in 78% yield in the form of an oil with a refractive index $n_D^{26}$ of 1.5820.

Analogously, the following compounds can be prepared:

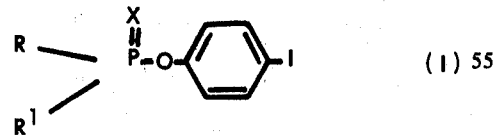 (1)

| Compound | X | R | R' | Yield (% of theory) | Physical constants (refractive index, melting point) |
|---|---|---|---|---|---|
| 2. | O | $iC_3H_7O$ | $iC_3H_7$ | 87 | $n_D^{26} = 1.5198$ |
| 3. | S | $iC_3H_7O$ | $iC_3H_7$ | 77 | m.p. 39°C |
| 4. | S | $CH_3$ | $C_2H_5O$ | 68 | $n_D^{26} = 1.5863$ |
| 5. | S | $C_2H_5$ | $C_2H_5O$ | 78 | $n_D^{24} = 1.5862$ |
| 6. | S | $C_2H_5$ | $iC_3H_7O$ | 87 | $n_D^{26} = 1.5700$ |
| 7. | S | $C_6H_5$ | $C_2H_5O$ | 73 | $n_D^{26} = 1.6158$ |
| 8. | S | $C_2H_5O$ | $iC_3H_7NH$ | 58 | $n_D^{26} = 1.5630$ |
| 9. | O | $(CH_3)_2N$ | $(CH_3)_2N$ | 71 | m.p. 67°C |
| 10. | S | $(CH_3)_2N$ | $(CH_3)_2N$ | 58 | m.p. 91°C |

It will be appreciated that the instant specification and examples are set forth by way of illustration and not limitation, and that various modifications and changes may be made without departing from the spirit and scope of the present invention.

What is claimed is:

1. An iodo-phenyl-thiono-phosphoric (phosphonic) acid ester or ester amide selected from the group consisting of
   O-isopropyl-O-(4-iodophenyl)-methanethionophosphonic acid ester,
   O-isopropyl-O-(4-iodophenyl)-ethanethionophosphonic acid ester, or
   O-ethyl-N-isopropyl-thionophosphoric acid ester amide.

2. The compound according to claim 1 wherein such compound is O-isopropyl-O-(4-iodophenyl)-methanothionophosphonic acid ester of the formula

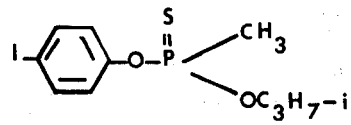

3. The compound according to claim 1 wherein such compound is O-isopropyl-O-(4-iodophenyl)-ethanethionophosphonic acid ester of the formula

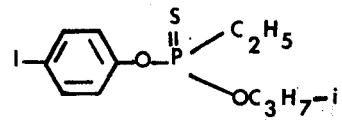

4. The compound according to claim 1 wherein such compound is O-ethyl-N-isopropyl-thionophosphoric acid ester amide of the formula

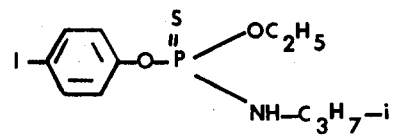

* * * * *